US00PP13284P2

(12) United States Plant Patent
Osiecki

(10) Patent No.: US PP13,284 P2
(45) Date of Patent: Nov. 26, 2002

(54) ANTHURIUM PLANT NAMED 'VALENTINE'

(75) Inventor: Marian Wincenty Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 0 days.

(21) Appl. No.: 09/960,455

(22) Filed: Sep. 24, 2001

(51) Int. Cl.[7] ..... A01H 5/00
(52) U.S. Cl. ..... Plt./365

(58) Field of Search ..... Plt./369, 365

*Primary Examiner*—Bruce R. Campell
*Assistant Examiner*—Annette H. Para

(57) ABSTRACT

A new and distinct cultivar of Anthurium is provided. It is a medium size plant, suitable for production in 15-cm to 20-cm containers, with relatively vigorous growth; full and symmetrical growth habit; early and abundant branching; early, very abundant and year-round flowering; and resistance to *Xanthomonas campestris* pv. *dieffenbachiae*. Dark red spathes with contrasting cream-colored spadices are held mostly above foliage.

3 Drawing Sheets

BOTANICAL CLASSIFICATION

Anthurium hybrid.

VARIETY DENOMINATION

'Valentine'.

BACKGROUND OF THE INVENTION

This invention relates to a new and distinct cultivar of anthurium plant, botanically known as Anthurium hybrid, and hereinafter referred to by the cultivar name Valentine.

The new cultivar is a product of a planned breeding program conducted by the Inventor in Altha, Fla. The objective of the program was to develop a well branching, compact pot Anthurium cultivar, resistant to *Xanthomonas campestris* pv. *dieffenbachiae*, with attractive spathes and a good flower count. The new Anthurium was discovered and selected by the Inventor in 1998 as a seedling within the progeny of a cross made in 1995 in a controlled environment in Altha, Fla. The female parent was a proprietary Anthurium seedling selection identified by the code number 91-11-48, obtained by the Inventor in the same breeding program, not patented. The male parent was a selected clone of Anthurium hybrid cultivar Lady Jane identified by the code number 941, not patented.

Asexual propagation of 'Valentine', since 1998, by means of tissue culture in Altha, Fla. has established that the unique characteristics of this new cultivar are in fact stable and reproduced true to type in successive generations.

SUMMARY OF THE INVENTION

The new Anthurium cultivar has not been observed under all possible environmental conditions. The phenotype may vary somewhat with variations in environment and/or horticultural practices such as temperature, light intensity, day length, fertilization, irrigation, propagation procedures etc., without any variance in genotype.

The following traits have been repeatedly observed and in combination distinguish 'Valentine' as a new and distinct cultivar of pot Anthurium:

1. Medium size plant, appropriate for 15-cm to 20-cm containers;

2. Symmetrical and full growth habit;
3. Relatively vigorous growth;
4. Abundant and relatively early branching;
5. Early, very abundant and year-round flowering;
6. Deep red, glossy spathes with contrasting cream-colored spadices held above foliage;
7. Very good inflorescence longevity on the plant;
8. Resistance to *Xanthomonas campestris* pv. *dieffenbachiae*.

Plants of 'Valentine' are distinguished from plants of the female parent, a proprietary Anthurium seedling selection identified by the code number 91-11-48, by its smaller size; earlier and more abundant branching; more abundant flowering; smaller leaf blades; much darker red, glossier, smaller, flatter, more horizontal spathes held closer to foliage; shorter, straight, cream-colored spadices as opposed to curved, dark purple spadices of 91-11-48; and greater inflorescence longevity on the plant.

Plants of 'Valentine' are distinguished from plants of the male parent, a selected clone of Anthurium hybrid cultivar Lady Jane identified by the code number 941, by its earlier and more abundant branching; earlier and more abundant flowering; smaller leaf blades; more ovate, shorter spathes, with lower length:width ratio, glossier, deep red and held above foliage as opposed to dark pink spathes of Lady Jane # 941, often held among foliage; cream-colored spadices as opposed to pinkish-cream spadices of Lady Jane # 941; and greater inflorescence longevity on the plant.

The new cultivar can be compared to its siblings, cultivars: 'Salsa' U.S. Plant patent application Ser. No. 09/960,456 and 'Favorita' U.S. Plant patent application Ser. No. 09/961,829. The comparisons were made on plants of the same age, grown side-by-side under the same greenhouse conditions in Altha, Fla.

Plants of the new Anthurium cultivar differ from plants of the cultivar Salsa in the following characteristics:

1. Plants of 'Valentine' are narrower, have taller foliage and fuller growth habit than plants of 'Salsa'.

2. Plants of 'Valentine' branch earlier and more abundantly than plants of 'Salsa'.

3. Plants of 'Valentine' start flowering later, but flower more abundantly than plants of 'Salsa'.

4. Leaf blades of 'Valentine' are smaller with lower length to width ratio than leaf blades of 'Salsa'.

5. Spathes of 'Valentine' are smaller, with lower length to width ratio and are held closer to foliage than spathes of 'Salsa'.

6. Spathes of 'Valentine' are deep red, whereas spathes of 'Salsa' are pink-red.

7. Spadices of 'Valentine' are smaller than spadices of 'Salsa'.

Plants of the new Anthurium cultivar differ from plants of the cultivar Favorita in the following characteristics:

1. Plants of 'Valentine' are smaller and have slightly fuller growth habit than plants of 'Favorita'.

2. Plants of 'Valentine' start flowering later, but flower more abundantly than plants of 'Favorita'.

3. Leaf blades of 'Valentine' are smaller, lighter green and less glossy than leaf blades of 'Favorita'.

4. Peduncles of 'Valentine' are thinner, weaker and shorter than peduncles of 'Favorita'.

5. Spathes of 'Valentine' are smaller, have lower length to width ratio; are held higher above foliage and have better longevity on the plant than spathes of 'Favorita'.

6. Spathes of 'Valentine' are deep red, whereas spathes of 'Favorita' are orange-red.

7. Spadices of 'Valentine' are smaller and cream-colored, whereas spadices of 'Favorita' are pink-purple.

The new cultivar can be compared to the known Anthurium cultivar '75-10', disclosed in U.S. Plant Pat. No. 9,355, a/k/a Red Hot™. The comparisons were made on plants of the same age, grown side-by-side under the same greenhouse conditions in Altha, Fla.

Plants of the new Anthurium cultivar differ from plants of the cultivar 75-10 in the following characteristics:

1. Plants of 'Valentine' are smaller and have smaller leaf blades than plants of '75-10'.

2. Inflorescences of 'Valentine' are of a good quality from the onset of flowering, whereas several first spathes produced by plants of '75-10' are very small and deformed.

3. Spathes of 'Valentine' are held closer to foliage, are more horizontal, flatter, less puckered, glossier and deeper red.

4. Spadices of 'Valentine' are shorter, straight and cream-colored, whereas spadices of '75-10' are usually curved and dark purple.

5. Inflorescences of 'Valentine' have greater longevity on the plant than inflorescences of '75-10'.

BRIEF DESCRIPTION OF THE PHOTOGRAPHS

The accompanying photographs illustrate the appearance of the new Anthurium cultivar, showing the colors as true as it is reasonably possible in color reproductions of this type. Colors in the photographs may appear slightly different from the color values cited in the botanical description, which accurately describe the actual colors of the plants of the new cultivar. The plant of 'Valentine' depicted in the photographs was approximately 15 months from planting a single tissue culture-produced microcutting, and was grown in a 15-cm container.

In the photographs:

BOTANICAL DESCRIPTION OF THE NEW CULTIVAR

Figure 1:
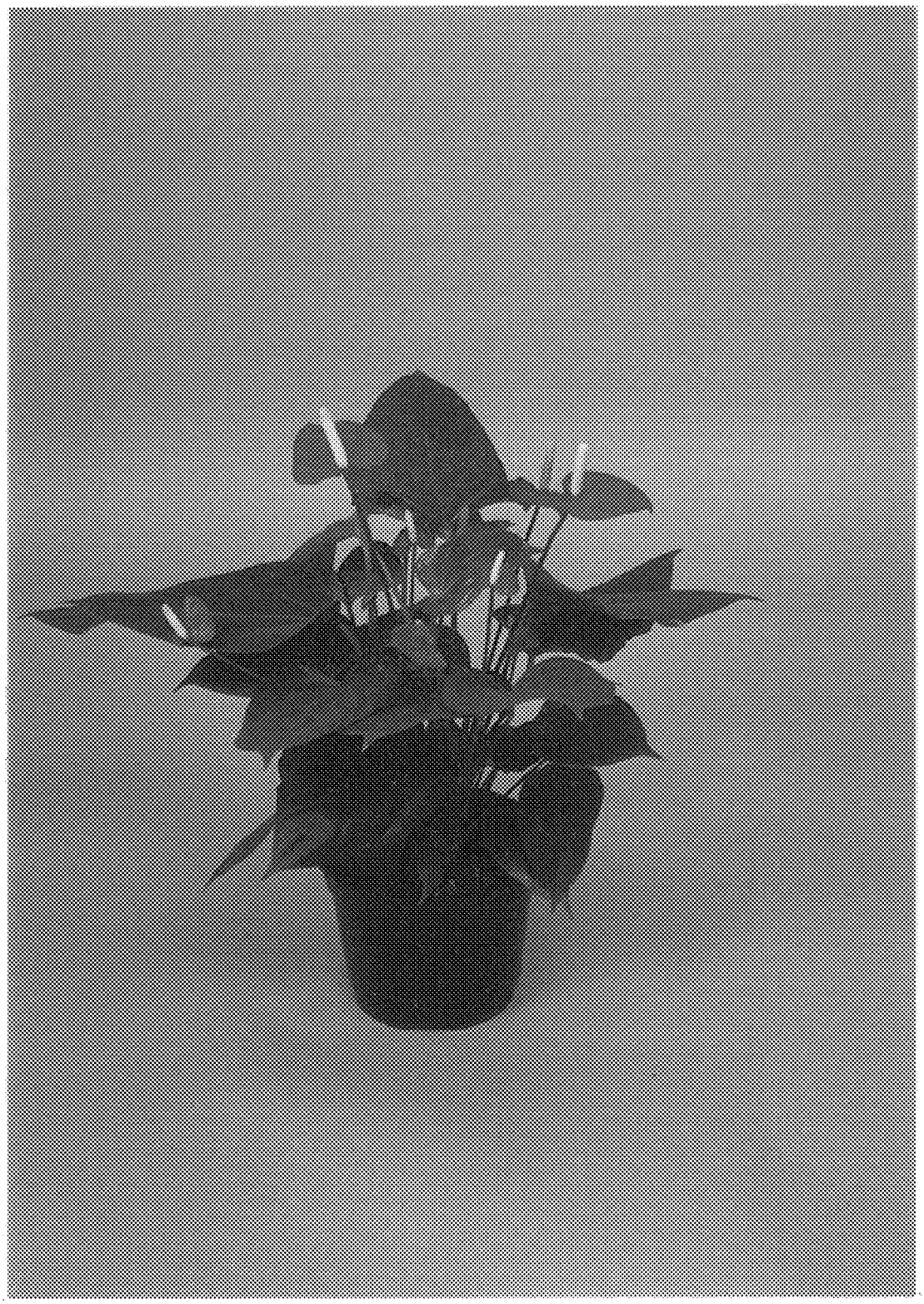
FIG. 1 depicts the whole plant.
Figure 2:
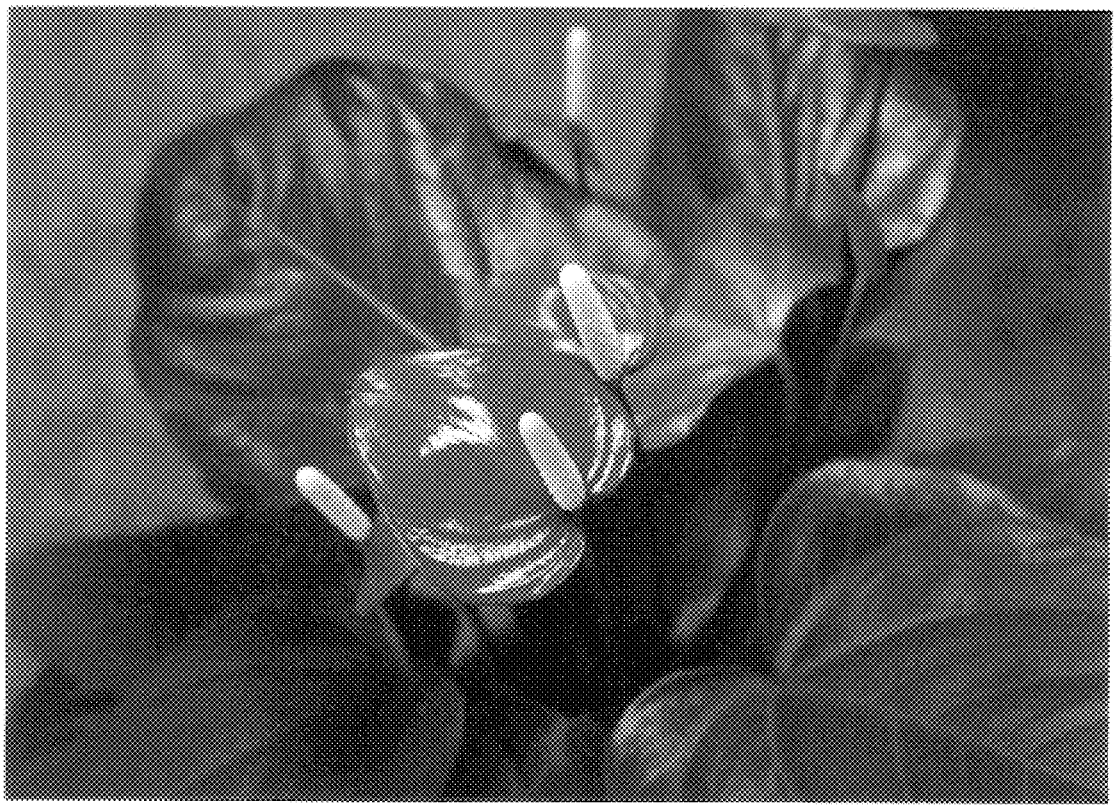
FIG. 2 illustrates the mature inflorescence.
Figure 3:
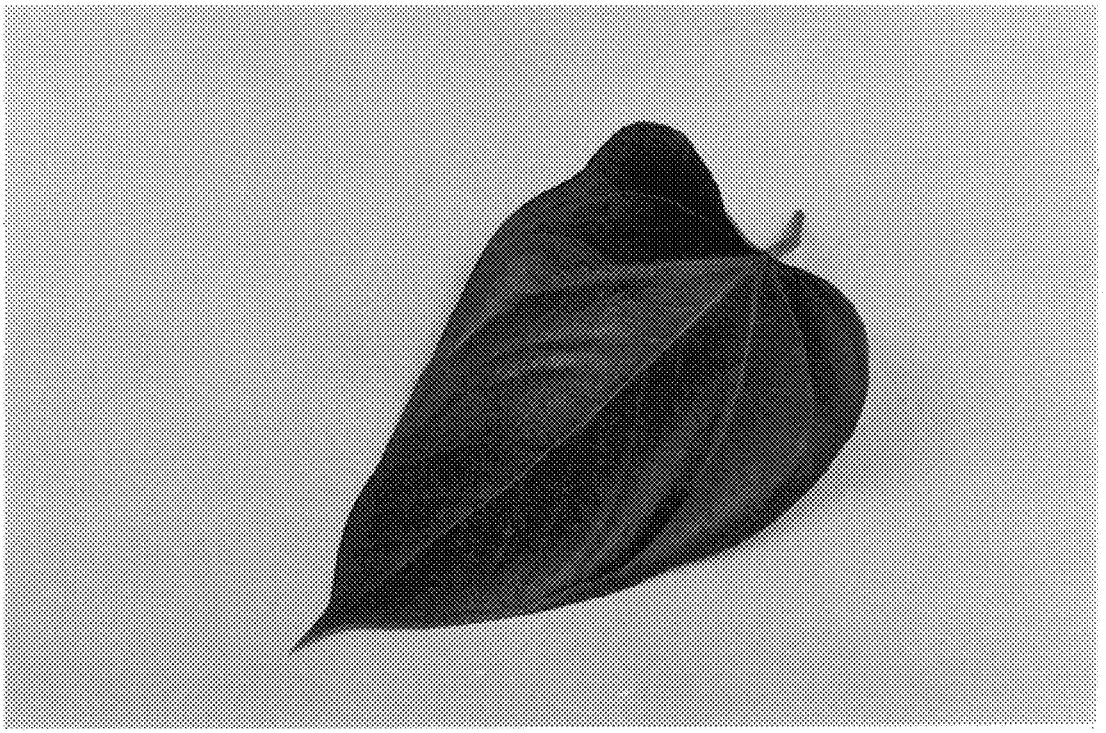
FIG. 3 illustrates the adaxial side of a mature leaf.
Figure 4:
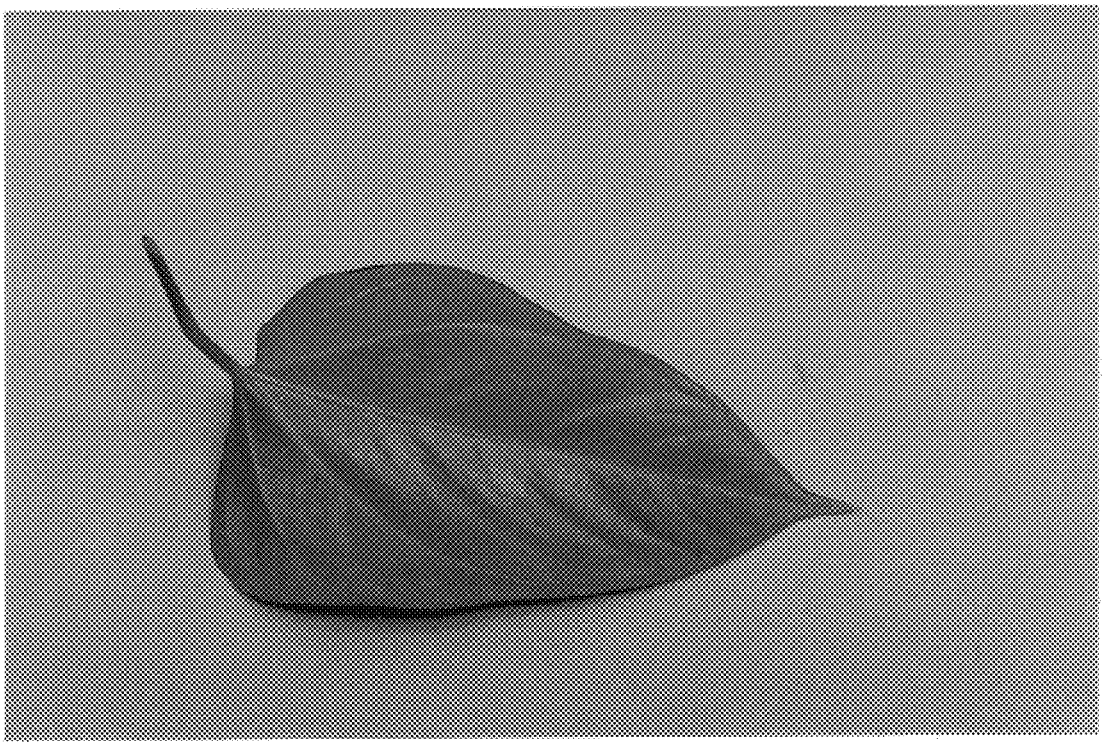
FIG. 4 illustrates the abaxial side of a mature leaf.

The following observations and measurements were recorded in February 2001, on plants grown in a polycarbonate-covered greenhouse in Altha, Fla. under conditions which closely approximate those used in commercial horticultural practice. During growth of these plants day temperature in the greenhouse ranged between 23 and 28° C., night temperature ranged between 20 and 23° C., and light level ranged between 800 and 1500 foot-candles. Plants used for these observations were grown as single plants in 15-cm containers and were about 15 months from planting tissue culture-produced microcuttings.

Mature, fully developed plants were used for the following observations and measurements unless otherwise indicated. Numerical measurements represent means from typical plants of 'Valentine'. Color references are made to The R.H.S. Colour Chart, except where general color terms of ordinary significance are used. Color values were determined under natural light of approximately 1200 to 2200 foot-candles.

Botanical classification: Anthurium hybrid cultivar Valentine.

Parentage:

*Female parent.*—Proprietary Anthurium seedling selection identified by the code number 91-11-48 (not patented).

*Male parent.*—Selected clone of Anthurium hybrid cultivar Lady Jane, identified by the code number 941 (not patented).

Propagation:

*Type.*—Plant tissue culture.

*Time to produce a rooted liner.*—Summer: About 13 to 14 weeks at about 25 to 30° C. soil temperature. Winter: About 15 to 16 weeks at about 22 to 27° C. soil temperature.

Plant description:

*Growth habit.*—Medium size, rounded, symmetrical, well-branched, full. Appropriate for 15-cm to 20-cm containers.

*Plant size.*—Height, soil level to top of inflorescences: About 39.7 cm. Height, soil level to top of leaf canopy: About 31.2 cm. Diameter (area of spread): About 41.6 cm.

*Plant vigor.*—Relatively vigorous.

*Crop time.*—About fourteen months are needed to produce a finished plant in a 15-cm container from a single tissue culture-produced microcutting.

Foliage description:

*Petiole.*—Size: About 14.5 cm long, about 3.6 mm in diameter immediately below geniculum. Geniculum: About 2.4 cm long, about 4.3 mm in diameter at the base. Inconspicuous. Color: Newly unrolled leaf, adaxial: Very variable due to variable amounts of purplish anthocyanin coloration. Varies between different combinations of 152A and 199A. Geniculum between 146A and 199A. Newly unrolled leaf, abaxial: Variable due to variable amounts of purplish anthocyanin coloration. Varies between different combinations of 152B and 199A. Geniculum 144A. Mature leaf, adaxial: Between 146B and 144A.

Amount of purplish anthocyanin coloration increases distally. Geniculum 146A with slight anthocyanin coloration. Mature leaf, abaxial: Approximately 144A near base; very slight purplish anthocyanin coloration in the distal part except for geniculum. Geniculum 144A.

*Leaf blade.*—Shape: Ovate; apex acuminate with some cuspidate tendencies; base truncate with cordate tendencies; margin entire. Size: About 17.3 cm long, about 11.3 cm wide; length:width ratio about 1.5:1. Aspect: Most leaves approximately horizontal. Texture/surface: Thick, leathery, glabrous; young leaves glossy. Venation: Pinnipalmate; primary veins prominent. Color: Newly unrolled leaf, adaxial: Usually greener and slightly darker than 146A with various amounts of purplish anthocyanin coloration along margin, on midrib and primary veins. Newly unrolled leaf, abaxial: Between 148A and 148B with fine line of purplish anthocyanin coloration along margin and various amounts of anthocyanin coloration on midrib and primary veins. Mature leaf, adaxial: Similar to 147A. Midrib and primary veins lighter (approximately 146A) with some purplish anthocyanin coloration near petiole juncture. Mature leaf, abaxial: Similar to 146B with a fine line of purplish anthocyanin coloration along margin. Midrib between 144B and 146D near petiole juncture; distally slightly darker, usually with increasing amounts of purplish anthocyanin coloration near apex. Some anthocyanin coloration usually present on primary veins near petiole juncture.

Inflorescence description:

*Inflorescence arrangement.*—Most spathes with spadices held above foliage. Most spadices in approximately straight line with peduncle.

*Flowering.*—Very abundant and year-round. Starts flowering naturally in 15-cm containers about 11 months after planting tissue culture-produced microcuttings. At 15 months about 11.0 inflorescences per plant, including buds.

*Spathe longevity.*—Exceptionally good. In spring spathe maintains color and gloss for approximately 3 months following bud appearance; after 4 months spathe still retains its ornamental value with various proportions between red and brownish and/or greenish color.

*Peduncle.*—Size: About 25.3 cm long, about 3.0 mm in diameter immediately below spathe. About 1.5 mm of peduncle between spathe and spadix base in front.

*Color.*—Mature inflorescence, front: Between 146A and 144A near base. Amount of purplish anthocyanin coloration increases distally. Approximately 42A immediately below spathe base. Mature inflorescence, back: Betweeen 144A, 146A and 146B near the base. Amount of purplish anthocyanin coloration increases distally. Approximately 45A immediately below spathe base. With age portions of peduncles above foliage often become brownish purple.

*Spathe.*—Shape: Wide ovate with some deltoid tendencies; apex between acuminate and aristate, short; base cordate; margin entire, slightly wavy, especially near base. Size: About 5.4 cm long, about 5.2 cm wide; ratio length:width about 1.1:1. Texture/Surface: Glabrous; exceptionally glossy; usually almost flat (not cupped); sometimes slightly puckered. Color: Closed bud (before unrolling): Between 53B and 46A. Newly unrolled spathe, front surface: Between 46A and 53A. Newly unrolled spathe, back surface: Between 53B and 46A with a darker margin (approximately 46A). Mature spathe, front surface: Between 53A and 46A. Mature spathe, back surface: Between 53B and 47A with a darker margin (approximately 46A).

*Spadix.*—Shape: Cylindrical, straight, slightly tapering at apex; cross section rounded. Size: About 3.2 cm long, about 7.4 mm in diameter. Flower density: About 15 to 17 flowers per linear 2 cm of spadix (mid-section). Color: Young, immediately after spathe unrolling: Varies between different combinations of 20B, 18A, 16B, 162A and 162B. Mature inflorescence: Proximal zone, with pistils similar to 159C. Distal zone, without pistils varies between different combinations of 162A, 162B, 20A, 20B, 19A, 18A, 16B, 16C, 15C, 14C and 13C.

*Botanical flower.*—Perianth: Perianth of an individual flower appears on the spadix surface as almost a diamond shape, about 2.5 mm long and 2 mm wide. Pistil: About 2.0 mm long and about 1.0 mm in diameter; protrudes fraction of a mm beyond perianth; cream-colored, translucent. Stigma small. Stamens: About 1.1 mm long and 0.9 mm wide; cream-colored, translucent; flat; firmly pressed against pistil. Do not protrude beyond perianth until pollen dehiscence. Pollen: Aging inflorescences produce small amounts of whitish pollen. Fragrance: Relatively strong, rather unpleasant.

*Fruit.*—Sometimes a few fruits spontaneously form on a spadix. Ripe fruit is ovoid, about 5 mm long and 3.5 mm wide. Color varies between different combinations of 163A, 163B, 28A, 28B and 26A.

*Seed.*—One seed per fruit. Seeds are ovoid, about 3 mm long and 2 mm wide.

Roots description: Relatively thick main roots, cream-colored with some purplish coloration and yellow root caps. Abundant, relatively thick, cream-colored lateral roots.

Disease and insect resistance: Plants of 'Valentine', which are grown in commercial greenhouses, have not shown any unusual susceptibility to pathogens or insects common to Anthurium. In the greenhouse test plants of 'Valentine' have demonstrated high degree of resistance to *Xanthomonas campestris* pv. *dieffenbachiae.*

I claim:

1. A new and distinct cultivar of Anthurium plant named 'Valentine' as described and illustrated herein.

* * * * *